(12) United States Patent  
Lancelin et al.

(10) Patent No.: US 7,374,722 B2  
(45) Date of Patent: May 20, 2008

(54) SYSTEM FOR TAKING A GAS SAMPLE ABLE TO CONTAIN PARTICLES OF SUSPENDED MATERIALS

(75) Inventors: Henri Lancelin, Morangis (FR); Gilles Guene, Levis Saint Nom (FR); Patrick Bleuse, Le Quesnoy (FR); Pierre Clausin, Ville d'Avray (FR)

(73) Assignee: Proengin SA, Cyr l'Ecole (FR)

( * ) Notice: Subject to any disclaimer, the term of this patent is extended or adjusted under 35 U.S.C. 154(b) by 284 days.

(21) Appl. No.: 10/117,089

(22) Filed: Apr. 8, 2002

(65) Prior Publication Data

US 2002/0146351 A1    Oct. 10, 2002

(51) Int. Cl.
- B32B 5/02    (2006.01)
- B32B 27/04   (2006.01)
- B32B 27/12   (2006.01)
- G01N 1/00    (2006.01)
- G01N 7/00    (2006.01)

(52) U.S. Cl. .............................. 422/83; 422/50; 422/58; 422/59; 422/94; 422/99; 422/100; 422/101; 422/102; 422/103; 422/104; 436/174; 436/177; 436/181; 73/1.01; 73/1.02; 73/23.2; 73/23.41

(58) Field of Classification Search .................. 422/50, 422/58, 59, 83, 94, 99, 100, 101, 102, 103, 422/104; 436/174, 177, 181; 73/1.01, 1.02, 73/23.2, 23.41
See application file for complete search history.

(56) References Cited

U.S. PATENT DOCUMENTS

| | | | | |
|---|---|---|---|---|
| 3,633,343 A | * | 1/1972 | Mark | 96/118 |
| 3,698,562 A | * | 10/1972 | Farrow et al. | 210/488 |
| 3,766,712 A | * | 10/1973 | Schaltenbrand | 95/68 |
| 3,859,065 A | * | 1/1975 | Schoeck | 55/378 |
| 5,605,553 A | * | 2/1997 | Connolly et al. | 55/487 |
| 5,800,597 A | * | 9/1998 | Perrotta et al. | 96/9 |
| 6,481,263 B1 | * | 11/2002 | Haley et al. | 73/23.41 |
| 6,497,753 B1 | * | 12/2002 | Gutmann | 96/55 |

* cited by examiner

*Primary Examiner*—Brian Sines  
(74) *Attorney, Agent, or Firm*—Browdy and Neimark, P.L.L.C.

(57) ABSTRACT

The sampling system of the invention includes a column comprising a first separator associated with a first collector so as to extract particles whose diameter is larger than a first diameter, and a second separator associated with a second collector which eliminates the finest particles and concentrates the other particles in the gas flow sucked up by the suction pipe of an analysis device.

4 Claims, 1 Drawing Sheet

SYSTEM FOR TAKING A GAS SAMPLE ABLE TO CONTAIN PARTICLES OF SUSPENDED MATERIALS

BACKGROUND OF THE INVENTION

1. Field of the Invention

The present invention concerns a system for taking a gas sample able to contain suspended materials, such as particles.

It applies in particular, but not exclusively, to the analysis of gas composition and/or to counting of particles present in this composition via a spectrographic analysis of the radiation produced by flame of a gas mixture including said composition.

2. Description of the Prior Art

It is known that this type of analysis is conducted by using a flame spectrophotometer including a burner in which combustion is provoked of a gas mixture flow comprising the gas composition to be analysed (for example ambient air) and hydrogen or other oxygen carrier so as to embody a flame whose light emissions are decomposable in a light spectrum whose spectrum lines are analysed so as to determine the nature and concentration of the sought-after elements.

The gas mixture flow is generated by creating a partial vacuum in the outlet circuit of the burner, for example by means of a turbine, sop as to provoke at the level of an intake circuit a sucking up of the gas composition to be sampled.

The advantage of this type of device resides in particular in that it makes it possible to conduct, not only the analysis of the gas composition, but also to determine the composition and the numeration of particles (for example bacteria or dust) present in this composition.

In fact on burning, these particles generate light impulses (flash) of limited duration able to count so as to obtain the number of particles per unit of volume of the gas composition to be analysed.

OBJECT OF THE INVENTION

More particularly, the object of the invention is to embody a system for sampling a gas composition able to be connected to the suction nozzle of a device of said type so as to be able to capture aerosols suspended in the composition and which is able to select the particles according to their shape and/or dimensions so as to only treat those particles whose size corresponds to the sought-after objects The object of the invention is also to embody a system of this type which makes it possible to conduct an omnidirectional sampling and which is designed so as to prevent the entering of projections projections (mud, pebbles) and insects.

SUMMARY OF THE INVENTION

According to the invention, so as to reach this result, the sampling system consists of a tubular column, preferably cylindrical, able to be connected via one of its extremities to the suction pipe of an analysis device and ending on the other side by a sampling head having a suction orifice opening outwardly.

According to the invention, said column successively includes starting from the head a first impact separator associated with a first collector so as to extract the particles whose diameter is greater than a first cut-off diameter and a second impact separator associated with a second collector which eliminates the finest particles and concentrates in the gas flow sucked up by the analysis device those particles whose diameter is greater than the cut-off diameter of this second impact separator.

Advantageously, the sampling head could include a coaxial cap to the column and having concavity orientated towards the column, this cap delimiting with a flange provided at the extremity of the column an annular space opening radially outwardly.

This annular space could advantageously have inside a radial plane an appropriate profile (for example in the shape of a chicane) so as to prevent the penetration of unwanted objects or material by constituting a light trap whilst favouring the flow of the gas stream containing the particles to be analysed and/or be counted.

BRIEF DESCRIPTION OF THE DRAWINGS

There now follows a non-restrictive example of one embodiment of the invention with reference to the accompanying drawings on which.

DESCRIPTION OF THE PREFERRED EMBODIMENTS

Figure 1:
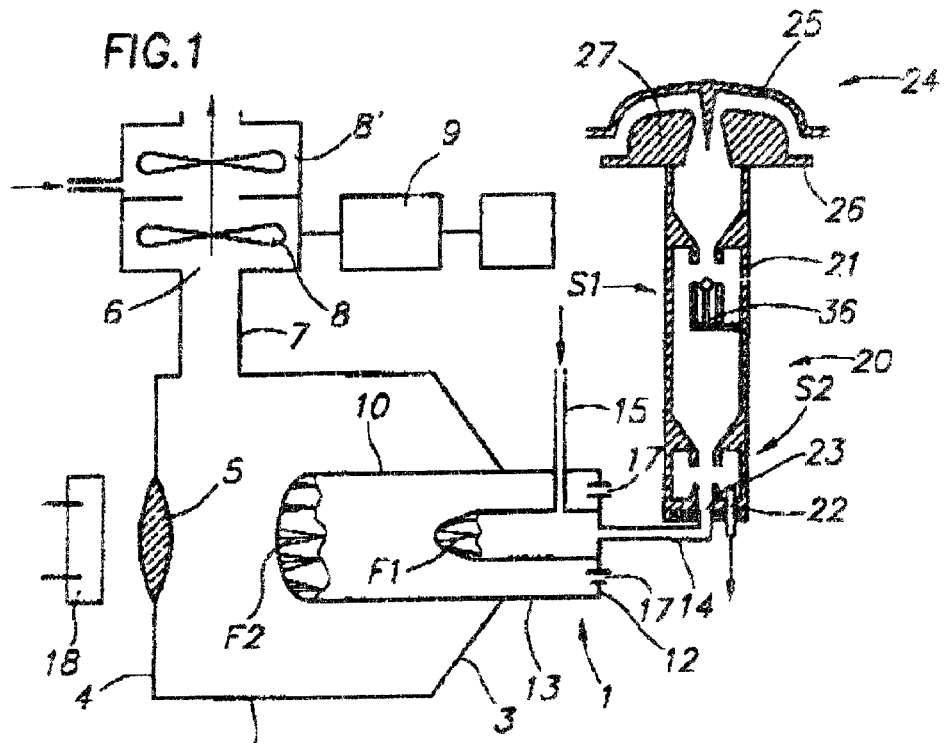
FIG. 1 diagrammatically represents a spectrophotometer equipped with a sampling system according to the invention.

In the example shown on FIG. 1, the spectrophotometer includes a burner 1 comprising two coaxial tubular combustion chambers axially offset with respect to each other, namely:

An external combustion chamber 2 closed on one side by a bottom 3 and on the other side by a covering cap 4 having a coaxial circular opening in which a lens 5 is mounted, this combustion chamber 2 having a lateral outlet circuit 6 connected to an outlet circuit 7 fitted with a turbine 8 activated by a motor, and An internal combustion chamber 10 having a diameter smaller than the external combustion chamber 2 and being engaged in the latter through an orifice provided in the bottom 3.

The chamber 10 can be made of a material including a reactive element. It opens inside the external chamber 2 opposite the lens 5 and at a specific distance from the latter. It is closed on the other side outside the chamber 2 by a bottom 12 on which a coaxial mixing nozzle 13 is mounted which extends over a fraction of the length of the chamber 10 and is connected firstly to a section pipe 14 for the gas to be analysed (which traverses the bottom 12), and secondly to a hydrogen injection pipe 15 which radially traverses the longitudinal wall of the chamber 10.

The functioning of this spectrophotometer is then the following:

The two chambers 2,10 are placed in a partial vacuum by the turbine 8 so as to provoke a sucking up of the gas to be analysed in the mixing nozzle Inside the nozzle 13, the flow of gas sucked up mixed with the injected hydrogen flow.

The difference between the outlet orifice of the nozzle 13 and the outlet orifice of the internal chamber 10 is calculated so that the mixture on fire leaving the nozzle 13 by producing a first flame $F_1$ sweeps the internal surface of the internal chamber 10 and reacts with the material of the latter inside a reactive zone of limited length.

Furthermore, this gas mixture receives a flow of air originating from calibrated orifices 17 provided in the bottom 12 of the chamber 10 around the mixing nozzle 13.

By means of this additional air, a second combustion is obtained at the outlet of the chamber 10, this second combustion generating a flame $F_2$ able to emit a light characteristic of the sought-after element which has reacted with the material of the internal wall of the internal chamber 10.

This light is then focussed by the lens 5 on an optoelectronic cell 18, possibly by means of a rotating filtering of a flame spectrometric device.

In accordance with invention, the intake pipe is connected to a sampling system 20 including a cylindrical tubular column 21 having one extremity being closed by a bottom 22 fitted with an orifice 23 to which the suction pipe 14 is connected, whereas the other extremity is fitted with an omnidirectional sampling head 24.

In this example, the sampling head 24 is composed of a flared cap 25 and a flange 26 closed on the extremity of the column 21 and comprising an axial protuberance 27 which slightly extends the flange 26 and whose profile inside an axial half-plane has an incurved shape 28 staring from the flange 26 approximately at ⅔rds of its width and which extends approximately exponentially up to a point 29 situated at a distance from the axis XX' of the column less than the radius of its internal cylindrical volume.

The circular edge of the protuberance 28 (location of points 29) is connected to the internal cylindrical surface of the column 21 by means of a conical portion 30 moving by bulging in the direction of the bottom 22.

The cap 25 includes a bulged from coaxial to the column and having inside an axial half-plane an exponential form which delimits with the exponential form of the protuberance a space E moving which gradually widens as it approaches the axis XX' of the column 21.

This bulged cap 25 outwardly includes an annular radial shoulder 31 extending parallel to the portion of the flange 26 which goes past the protuberance 27, this forming with the latter an omnidirectional annular orifice OP for sampling the gas composition to be analysed which extends along a radial plane of symmetry.

Advantageously, at the level of its joining point with the flange 26, the protuberance 27 extends axially, that is perpendicular to the radial plane of symmetry of the orifice OP. By means of this arrangement, an impact separator is obtained which ensures that projections of undesired materials are unable to penetrate inside the column 21 by disturbing the functioning of the sampling system and/or the analysis device.

Moreover, the cap 25 comprises a coaxial conical form 33 extending from the central region of its concave face by delimiting with the conical portion 30 of the protuberance 27 a space widening towards the bottom of the column.

The column 21 includes two successive separators, namely a first separator $S_1$ comprising an impact separator situated in the central portion of the column, and a second separator $S_2$ comprising a virtual impact separator situated close to the bottom 22.

The first separator $S_1$ introduces a truncated deflector 34 which reduces the passage section of the cylindrical column 21 in the direction of the bottom 22. This deflector 34 is extended by an axial shoulder 35 orientated towards the bottom 22. This shoulder 35 defines a cylindrical axial passage with a small diameter below which and at a predetermined distance an impact separator $I_1$ is placed.

This impact separator $I_1$ is composed of a coaxial cylindrical collector 36 having the same diameter as the shoulder 35. This collector 36 contains a flared impact head 37 borne by a coaxial rod 38, the diameter of the head 37 being larger than that of the rod 38.

The head 37 is situated below the orifice of the collector 36 which comprises above the head 37 a slight bore narrowing.

The second separator $S_2$ also introduces a conical deflector 39 which reduces the passage section of the column 21 in the direction of the bottom 22 and which delimits with the lower portion of the column 21 an annular concavity $CA_1$ orientated towards the bottom 22.

This deflector 39 cooperates with a second coaxial deflector 40 situated above and which with the column 21 delimits an annular concavity $CA_2$ orientated towards the sampling head 24.

This deflector 40 delimits around the central axis of the column 21 a central passage 41 widening towards the bottom and communicating with the suction pipe 14 of the spectrophotometric device.

The two concavities $CA_1$, $CA_2$ constitute an annular extraction chamber opening towards the axis of the column 21 via an annular orifice.

This extraction chamber is connected to suction means, for example a suction stage 8' of the turbine 8.

The functioning of the suction system is thus the following:

The suction generated by the turbine 8 is such that the flow sucked up by the stage 8' is about 90% of the flow circulating in, the column (par example, between 12 and 18 l/min), whereas the suction pipe flow 14 only represents 10% (par example, between 1, 3 and 2 l/min).

Under the effect of this suction, an omnidirectional sampling of gas charged with particles is obtained through the sampling orifice OP of the head 24.

Figure 2:
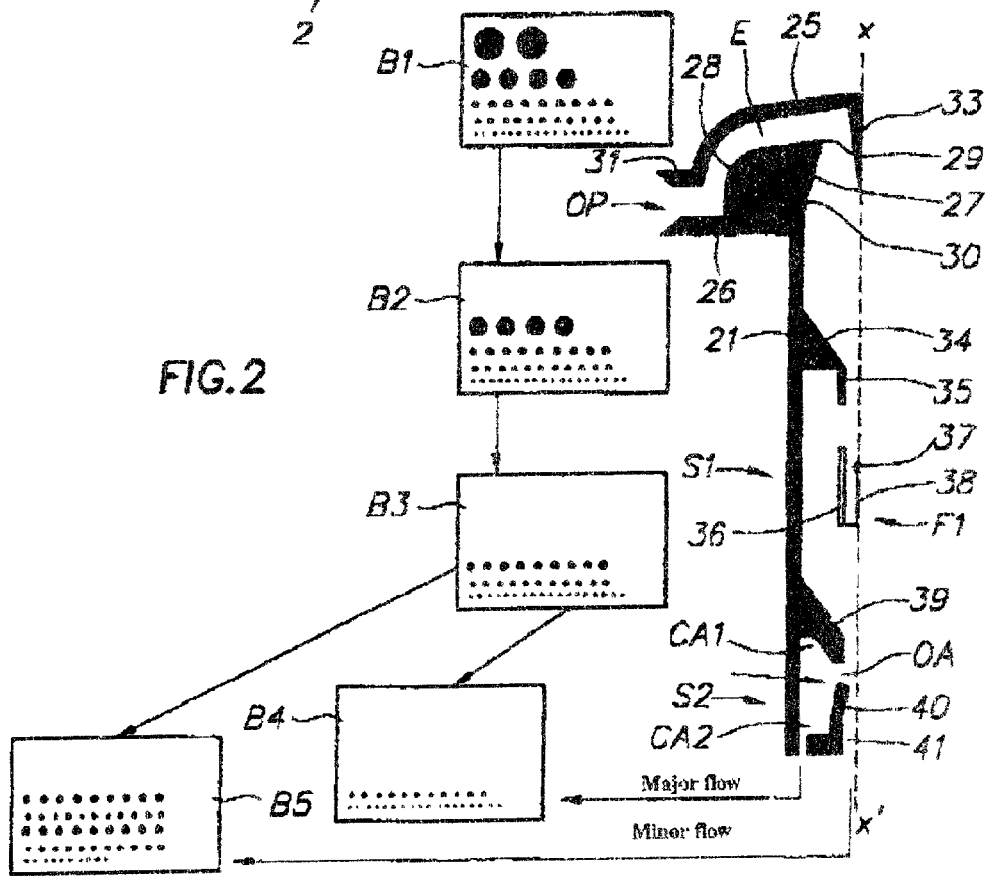
FIG. 2 is an axial cutaway view of the sampling system shown on FIG. 1.

On FIG. 2, the block $B_1$ diagrammatically shows particles of various diameters, the largest (pebbles or insects) stopping on the axial form of the protuberance 27 and are rejected outside. The particles of smaller diameter (block $B_2$) are driven by the gas flow in the sinuous path of the head 24 and are concentrated towards the axis XX' of the column 21 on leaving this path by means in particular of the conical portion 33. The particular form of the sinuous path borrowed by the gas forms a light trap to ensure that the optical detector of the analysis device is not blinded by daylight.

On passage at the level of the separator $S_1$, the particles are first of all concentrated by the deflector 34 and then the finest particles are sucked up into the annular passage between the column 21 and the collector 36.

The largest particles larger than the cutoff diameter $\phi C_1$ of the impact separator continue their axial path so as to stop on the head 37 and be stored in the collector 36 (the head 37 then acting a role similar to that of a valve).

The gas flow whose largest particles have been extracted (block $B_3$) are again recentered by the deflector 39, whereas the extremely fine particles (smaller than the cutoff diameter $\phi C_2$ of the impact separator) (block $B_4$) are sucked up by the vacuum stage 8'. The rest of the particles (block $B_5$) whose diameter $\phi C_3$ is between the cutoff diameters $\phi C_1$ and $\phi C_2$ is sucked up by the suction pipe of the analysis device.

Of course, the shapes and dimensions of this sampling system could be adapted so that the diameters of the sample particles correspond to those of the particles it is desired to analyse.

The invention claimed is:

1. System for taking a gas sample likely to contain particles of suspended materials for which it is desired to count and/or be analysed by means of an analysis device including a suction pipe for sucking up said sample, said system comprising a tubular column delimiting a passage section and said column having a bottom connected to said suction pipe and a sampling head located opposite to said bottom, wherein said column successively comprises starting from said head a first impact separator having a first truncated deflector which reduces said passage section in the direction of said bottom and a collector provided with and impact head situated below said deflector in a central part of said column to extract particles whose diameter is larger than a first diameter and a second separator located below said first impact separator and comprising a second deflector which reduces said passage section in the direction of said bottom and a second collector comprising an annular extraction chamber having an annular opening located below said second deflector and debouching in said column to eliminate the finest particles whose diameter is smaller than a second cut-off diameter and to concentrate in a gas flow sucked up by said suction pipe particles having a diameter larger than said second cut-off diameter.

2. System according to claim 1, wherein said first truncated deflector is fitted with an axial shoulder, and said collector has a coaxial cylindrical shape situated below said shoulder and at predetermined distance from the latter, this collector containing a bulged impact head borne by a coaxial rod.

3. System according to claim 2, wherein said head of the impact separator is situated below the orifice of the collector which comprises above the head a slight bore narrowing.

4. System according to claim 1, wherein the second separator introduces firstly a first conical deflector which reduces the passage section of the column in the direction of the bottom and with delimits with the lower portion of the column a concavity orientated towards the bottom, and secondly a second coaxial deflector situated below the first which delimits with the column a concavity orientated towards the sampling head, this deflector delimiting around the central axis of the column a central passage widening towards the bottom in communication with said suction pipe, in that the tow concavities constitute an extraction chamber opening towards the axis of the column by an annular orifice, and wherein this extraction chamber is connected to suction means.

* * * * *